US00PP08393P

United States Patent [19]

Zaiger et al.

[11] Patent Number: Plant 8,393

[45] Date of Patent: Sep. 28, 1993

[54] INTERSPECIFIC TREE "TRI-LITE"

[76] Inventors: Chris F. Zaiger, 537 Rosemore Ave.; Gary N. Zaiger, 1907 Elm Ave.; Leith Marie Gardner, 1207 Grimes Ave.; Grant G. Zaiger, 4005 California Ave., all of Modesto, Calif. 95351

[21] Appl. No.: 997,509

[22] Filed: Dec. 28, 1992

[51] Int. Cl.[5] ..... A01H 5/00

[52] U.S. Cl. ..... Plt./42.1

[58] Field of Search ..... Plt./38.1, 42.1

*Primary Examiner*—James R. Feyrer

[57] ABSTRACT

Our new development relates to a distinct variety of interspecific tree (peach×plum peach), which as the following unique combination of desirable features:

1. The ability to be a regular and productive bearer of medium size fruit.
2. Fruit having very firm white flesh with good handling and shipping quality.
3. Fruit with good flavor and eating quality both fresh and canned.
4. Fruit that will maintain excellent texture, shape and appearance after being canned.
5. The ability of the fruit to stay firm on the tree 12 to 15 days after maturity (shipping ripe).
6. After being canned, the fruit having a very attractive clear white flesh color.

1 Drawing Sheet

ORIGIN OF THE VARIETY

The present new and distinct variety of interspecific tree (peach×plum peach) was originated by us in our experimental orchard located near Modesto, Calif. as a first generation seedling from a cross between a selected seedling with the identification number 23EA103 and mixed pollen from three plum peach selections. The female parent 23EA103 originated as a selected seedling grown from seed of an open pollinated O'Henry Peach (U.S. Plant Pat. No. 2,964). The mixture of pollen used for this cross was collected from 3 interspecific (plum×peach) trees with the identification numbers 4G946, 4G816 and 4G1008. The three interspecific (plum×peach) trees have a common female parent Red Beaut Plum (U.S. Plant Pat. No. 2,539) crossed with each pollen of unknown parentage.

ASEXUAL REPRODUCTION OF THE VARIETY

The new and distinct variety of interspecific tree (peach×plum peach) was asexually reproduced by budding, as performed by us in our experimetnal orchard located near Modesto, Calif. and shows that all characteristics run true to the original tree and are established and transmitted through succeeding propagations.

SUMMARY OF THE VARIETY

The new and distinct variety of interspecific tree (peach×plum peach) which is of large size, vigorous upright in growth and a regular and productive bearer of medium size, while flesh clingstone fruit with good flavor and eating quality both fresh and canned. The present variety of interspecific tree (peach×plum peach) is further characterized as to its novelty by producing very firm white flesh fruit that will stay firm on the tree 12 to 15 days after maturity (shipping ripe) and after being canned, maintain excellent texture and shape with an attractive clear white flesh color.

BRIEF DESCRIPTION OF THE PHOTOGRAPHS

The accompanying color photographic reproductions show typical specimens of the foliage and fruit of our new interspecific variety (peach×plum peach), with the upper and lower surface of the leaves being illustrated, also with an exterior and sectional view of the fruit being divided in the suture plane to reveal flesh coloration and a stone remaining in place. The photographs were taken shortly after the fruit was picked (firm ripe) and the colors are as nearly true as is reasonably possible in a color representation of this type.

DESCRIPTION OF THE VARIETY

The following is a detailed botanical description of our new and distinct variety of interspecific tree, its flowers, foliage and fruit as based on observations of specimens grown near Modesto, Calif., with color terminology (except those in common terms) in accordance with Reinhold Color Atlas by A. Kornerup and J. H. Wanscher.

Tree:
- *Size.*—Large.
- *Vigor.*—Vigorous.
- *Form.*—Upright.
- *Density.*—Medium dense.
- *Shape.*—Normally pruned to vase shape.
- *Production.*—Productive.
- *Bearer.*—Regular.

Trunk:
- *Size.*—Medium stocky.
- *Surface.*—Medium shaggy.
- *Color.*—Brown to dark brown (6-E-5) to (6-F-5).

Branches:
- *Size.*—Medium to large.
- *Surface.*—Smooth to medium rough.
- *Lenticels.*—Medium number Medium size.
- *Color.*—Brown to grayish brown.

Leaves:
- *Size.*—Medium. Average length — 5". Average width — 1½".
- *Form.*—Lanceolate.
- *Texture.*—Smooth.
- *Margin.*—Crenate.
- *Thickness.*—Medium.

*Petiole.*—Average length — $\frac{5}{8}$". Medium thickness.

*Glands.*—Reniform. Small to medium size. Number varies from 2 to 4. Average number 2. Positioned on base of leaf blade and upper porton of petiole.

*Color.*—Upper surface — green to dark green (25-F-8) to (26-F-8). Lower surface — dull green to green (25-E-4) to (26-F-6).

Flower buds:

*Size.*—Medium.

*Form.*—Plump.

*Length.*—Medium.

*Pubescence.*—Pubescent.

Flowers:

*Size.*—Large — showy.

*Blooming period.*—Mar. 4, 1992 to Mar. 11, 1992. Varies slightly with climatic conditions.

*Pollen.*—Present.

*Color.*—Pink.

Fruit:

*Maturity when described.*—Firm ripe.

*Date of first picking.*—Jun. 20, 1992.

Date of last picking.—Jun. 28, 1992.

*Size.*—Medium. Average diameter axially — $2\frac{3}{8}$" to $2\frac{1}{2}$". Average transversely in suture plane $2\frac{3}{4}$" to 3".

*Form.*—Nearly globose — slightly flattened at the apex and stem end.

*Suture.*—Shallow — nearly smooth, extends from base to apex.

*Cavity.*—Rounded, to slightly elongated in suture plane. Average depth — 7/16". Average breadth — $\frac{3}{4}$".

*Base.*—Retuse.

*Apex.*—Retuse, varies from round to retuse.

Flesh:

*Texture.*—Very firm.

*Fibers.*—Few — tender.

*Juice.*—Moderate.

*Ripens.*—Evenly.

*Flavor.*—Good — mild — sweet — subacid.

*Aroma.*—Slight.

*Eating quality.*—Good.

*Color.*—White (1-A-1). Pit cavity — white to off white — clear white after being canned.

Skin:

*Thickness.*—Medium.

*Texture.*—Medium.

*Tendency to crack.*—None.

*Down.*—Moderate. Very short.

*Color.*—White to pinkish white ground color (8-A-1) to (8-A-2) Overspread with red blush (11-A-8) to (11-B-7).

Stone:

*Type.*—Clingstone.

*Size.*—Medium to large. Average length — $1\frac{1}{4}$". Average width — $1\frac{1}{4}$". Average thickness — $\frac{1}{2}$".

*Form.*—Oval.

*Base.*—Usually rounded — varies from rounded to straight.

*Sides.*—Usually unequal with slight narrow ridge forming on suture side of stone. Varies from equal to unequal.

*Apex.*—Cuspidate.

*Surface.*—Furrowed toward apex — pitted throughout — heavier toward base.

*Tendency to split.*—Very slight.

*Color.*—Brown to reddish brown (9-E-5) to (10-E-5).

Use: Dessert.

*Market.*—Local and long distance. Canned.

Keeping quality: Good.

Shipping quality: Good.

The present variety of interspecific tree (peach×plum peach), its foliage, flowers and fruit herein described may vary in slight detail due to cultural practices, soil types and climatic conditions under which the variety may be grown; the present description being of the variety grown by us under the ecological conditions prevailing near Modesto, Calif.

We claim:

1. A new and distinct variety of interspecific tree. (peach×plum peach), substantially as illustrated and described, characterized by its large size, vigorous upright growth and a regular and productive bearer of medium size, white flesh, clingstone fruit with good flavor and eating quality both canned and fresh; the fruit is further characterized by having very firm flesh and the ability to hold firm on the tree 12 to 15 days after maturity (shipping ripe) and after being canned maintains excellent texture and shape with an attractive clear white flesh color.

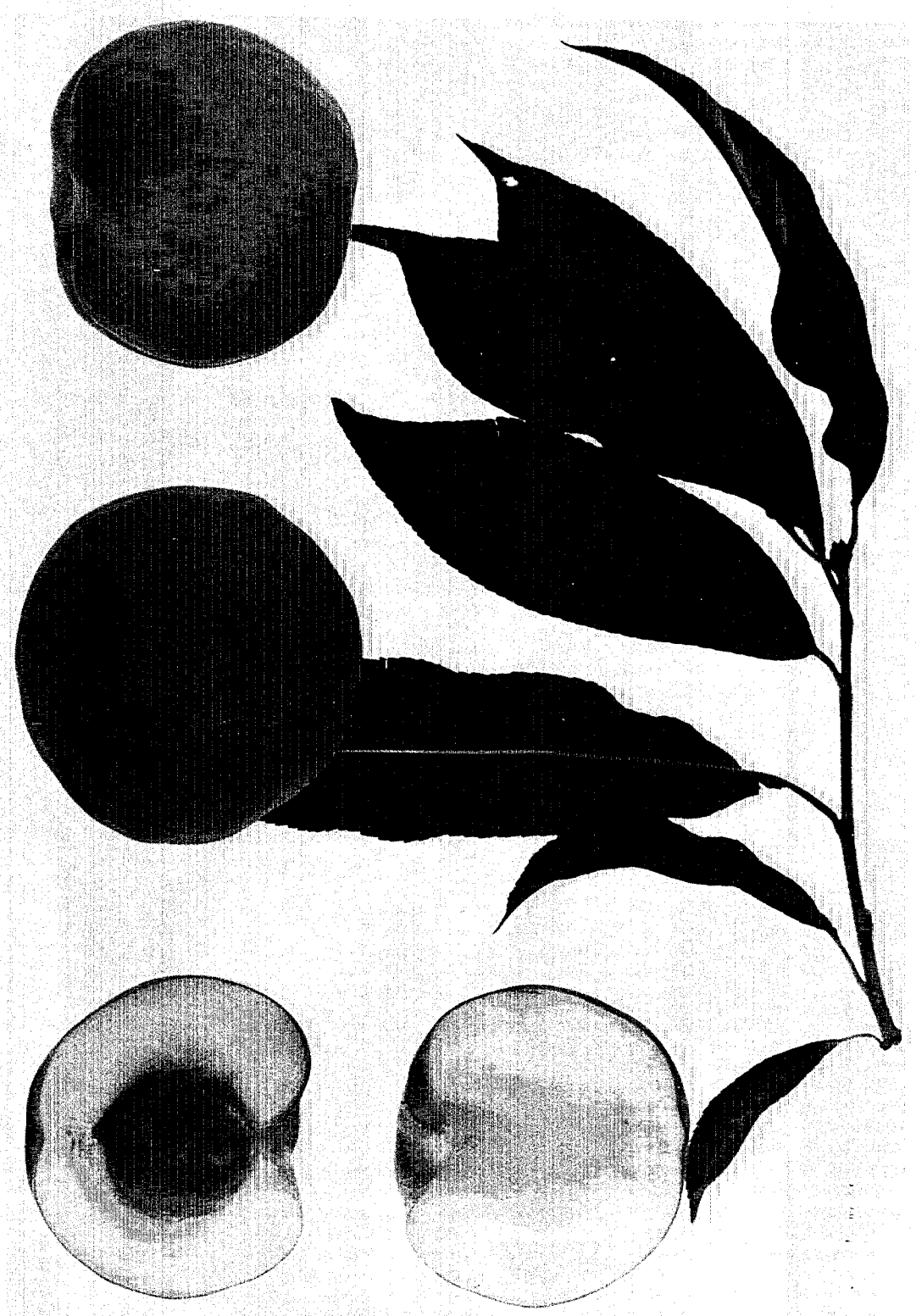

* * * * *